(12) United States Patent
Ogram

(10) Patent No.: US 10,850,001 B1
(45) Date of Patent: Dec. 1, 2020

(54) STERILIZING MECHANISM

(71) Applicant: Mark Ellery Ogram, Tucson, AZ (US)

(72) Inventor: Mark Ellery Ogram, Tucson, AZ (US)

(*) Notice: Subject to any disclaimer, the term of this patent is extended or adjusted under 35 U.S.C. 154(b) by 0 days.

(21) Appl. No.: 16/873,580

(22) Filed: May 11, 2020

(51) Int. Cl.
*A61L 9/20* (2006.01)

(52) U.S. Cl.
CPC ............ *A61L 9/20* (2013.01); *A61L 2209/111* (2013.01); *A61L 2209/12* (2013.01)

(58) Field of Classification Search
CPC ........ A61L 2/10; A61L 9/20; A61L 2209/111; A61L 2209/12; A61L 2209/134
See application file for complete search history.

(56) References Cited

U.S. PATENT DOCUMENTS

| | | | | |
|---|---|---|---|---|
| 6,893,610 B1* | 5/2005 | Barnes | ............. | A61L 9/015 422/121 |
| 8,440,143 B2* | 5/2013 | Liptak | ............. | A61L 9/205 422/186.3 |
| 10,258,715 B1* | 4/2019 | Collins | ............. | H01L 33/32 |
| 2004/0166018 A1* | 8/2004 | Clark | ............. | A61L 9/205 422/4 |
| 2006/0057020 A1* | 3/2006 | Tufo | ............. | A61L 9/20 422/24 |
| 2009/0217690 A1* | 9/2009 | Silderhuis | ............. | A61L 9/205 62/264 |
| 2010/0047116 A1* | 2/2010 | Garner | ............. | A61L 9/015 422/4 |
| 2013/0239803 A1* | 9/2013 | Palmer | ............. | A61L 9/20 95/22 |
| 2017/0007736 A1* | 1/2017 | Engelhard | ............. | B01D 53/864 |
| 2017/0296299 A1* | 10/2017 | Yun | ............. | B65B 43/00 |
| 2018/0133355 A1* | 5/2018 | Kirschman | ............. | A61L 9/18 |

FOREIGN PATENT DOCUMENTS

CN 106975094 A * 7/2017

* cited by examiner

*Primary Examiner* — David E Smith

(57) ABSTRACT

An air sterilizing apparatus is created which can be set within an environment without adversely affecting people, pets, or plants within the environment such as a room. The apparatus uses a passage through which ambient air passes. The passage has a treatment chamber in which ultraviolet light (ideally UV-C) is used to sterile the ambient air. Each end section of the passage is configured to block light from exiting the passage. In the preferred embodiment, each end section includes a coating of UV adsorbing material to provide further protection to the environment from the UV light.

14 Claims, 2 Drawing Sheets

STERILIZING MECHANISM

BACKGROUND OF THE INVENTION

At the present time, and into the foreseeable future, there is a significant need to provide protection to the populace from air borne and contact pathogens such as bacterium and viruses. A variety of chemicals and treatments have been developed which are used to protect the populace.

It has long been known that ultraviolet (UV) light has the affect of sterilizing bacterium and if emitted in certain wave lengths (UV-C) can even sterilize viruses. Unfortunately, UV-C is also harmful to humans, pets, and plants so must be used only when the area is isolated. Typically, a UV-C generating apparatus is placed within a vacant room, the windows are blocked, and then the UV-C generator is activated for a period of time. This methodology is used in operating rooms overnight to sterilize the operating room when not in use.

Such UV generators are described in: U.S. Pat. No. 10,221,081, entitled "UV Sensor" issued to Kruger et al. on Mar. 5, 2019; U.S. Pat. No. 10,583,212, entitled "Portable UV-C Disinfection Apparatus, Method and System" issued to Ufkes on Mar. 10, 2020; U.S. Pat. No. 10,556,025, issued to Ufkes on Feb. 11, 2020; U.S. Pat. No. 10,441,671, entitled "Disinfecting Apparatus" issued to Sobhy et al. on Oct. 5, 2019; U.S. Pat. No. 10,376,604, entitled "Sterilization Units, Systems, and Methods" issued to Romo et al. on Aug. 13, 2019; and U.S. Pat. No. 10,265,540, entitled "Mobile Device Case with Ultraviolet Light Sanitizer and Light Therapy" issued to Yehezkel on Apr. 23, 2019; all of which are incorporated hereinto by reference.

As noted, UV-C has some significant disadvantages which means the technology cannot be used in a continuous manner within a room which might be habituated. For this reason, the use of UV and UV-C has been significantly limited.

It is clear there is a need for a continuously operating sterilizer.

SUMMARY OF THE INVENTION

An air sterilizing apparatus is created which can be operated within an environment, such as a diner or theatre, without adversely affecting people, pets, or plants within the room. The apparatus uses a passage through which ambient air passes. The passage has a treatment chamber in which ultraviolet light (ideally UV-C) is used to sterilize the ambient air. Each end section of the passage is configured to block light from exiting the passage.

In the preferred embodiment, each end section also includes a coating of UV adsorbing material to provide further protection to the environment from the UV light. This provides assurance that UV light is not escaping to adversely affect people.

The ideal UV applied is UV-C which has been shown to have the desired effect on viruses and bacterium. Other UV light wave lengths are obvious to those of ordinary skill in the art.

Because of this structure, more powerful UV light may be used without fear. The present invention provides a sterilizing unit which is capable of being used among humans, plants, and animals.

To accomplish its objectives, the apparatus provides for a chamber through which ambient air is pulled. The ambient air passes by an Ultra-violet (UV) light to neutralize viruses and bacterium. The preferred UV light is in the UV-C range to sanitize a broad range of bacterium and viruses. The UV light is contained within the chamber and through the use of baffles at the ends and the like to prevent the UV light from escaping the chamber.

Further embodiments place, at the both ends of the chamber, a coating of a UV adsorbing material is add for further protection from accidental exposure to the UV. Even a black coating has some of the desired affects.

Those of ordinary skill in the art readily recognize a variety of UV adsorbing materials which can be used in this context, including, but not limited to: U.S. Pat. No. 10,605,813, entitled Ultraviolet Absorbing Polymeric Dyes and Methods for Using the Same" issued to Lian et al. on Mar. 31, 2020; U.S. Pat. No. 10,428,236, entitled "Polyurethane Urea Resin Composition Exhibiting UV-Absorption-Agent Resistance, Moulded Body Using said Composition, and Coating Material" issued to Kawaguchi et al. On Oct. 1, 2019; and U.S. Pat. No. 10,228,375, entitled "Ultraviolet Absorbing Polymeric Dyes and Methods for Using the Same" issued to Liang et al. on Mar. 12, 2019; all of which are incorporated hereinto by reference.

In one embodiment of the invention the interior of the treatment chamber is mirrored or UV-reflective so that the UV light is maximized to obtain maximal disinfecting capability. This also provides maximal saturation for the ambient air.

In another embodiment of the invention, the UV light is focused through the use of a prism or lens to concentrate the UV affect onto a selected area through which the ambient air passes. By concentrating the UV light, a much wider range of sterilization is obtained.

Another embodiment of the invention addresses the sterilization of surfaces by providing for the treatment chamber to be openable (either automatically or by remote control) to expose the UV light to the room when it is vacated. In this manner, the room is subjected to enhanced sterilization when not occupied.

In this embodiment, there is preferable an alarm, either visual or auditory so that humans are warned of the situation.

Another enhancement for this aspect is the use of a motion sensor which curtails operation of the UV generator when the chamber is open and motion is sensed in the room. This prevents humans or animals from accidentally being exposed to the UV.

Those of ordinary skill in the art readily recognize a variety of mechanisms which can be used in this context, including, but not limited to: U.S. Pat. No. 10,634,299, entitled "Motion Sensor Based Lighting Fixture Operation" issued to Wright et al. on Apr. 28, 2020; and U.S. Pat. No. 10,645, entitled "Smart Motion Detection Device and Related Determining Method" issued to Yet et al. on May 5, 2020; both of which are incorporated hereinto by reference.

By allowing the opening of the treatment chamber to expose the entire room, surfaces are also sterilized. In the example of a diner, operating during the day, the apparatus sterilizes the air to reduce the chance of infection; at night when the diner is closed, the open treatment chamber exposes all of the surfaces to sterilize them as well so that when the diner again opens. The entirety of the diner is sterilized for use.

In another aspect of the invention, a number of treatment chambers are used into which ambient air is trapped and treated for the desired dwell time before the now-treated air is released back into the room. This aspect of the invention provides for expanded dwell time for the ambient air being exposed to the UV light. The preferred embodiment uses multiple transparent channels (ideally glass) passing through the treatment chamber allowing the UV source to treat all the air within the channels. Ambient air is drawn into a channel and the channel is then closed (either at the entry or the exit end) causing the ambient air to stop movement for the desired dwell time. While one channel is closed, another (which has already been treated) is opened to be exhausted into the room.

The opening/closing of the channel is ideally done using a rotating baffle which opens or closes a channel for the desired time. Those of ordinary skill in the art recognize a variety of other mechanisms which will accomplish this goal.

Another technique to provide the dwell time is to either use a fan or a baffle which temporarily stops the airflow through the treatment chamber. In this manner, the dwell time may be adjusted to the desired level.

The invention together with various embodiments thereof will be more fully explained by the accompanying drawings and the following description thereof.

DRAWINGS IN BRIEF

DRAWINGS IN DETAIL

Figure 1A:
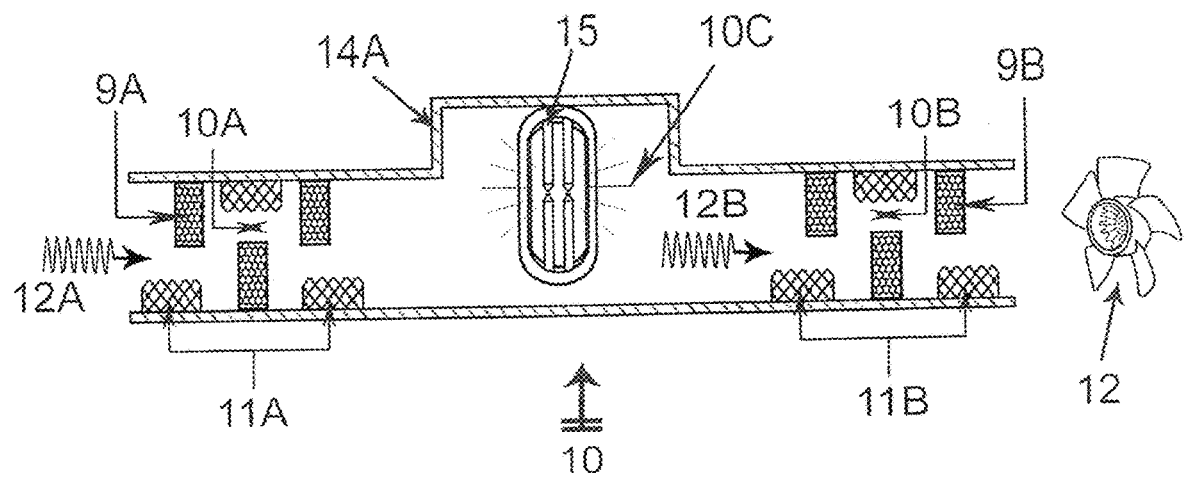
FIGS. 1A and 1B illustrate the preferred embodiment of the invention.
Figure 1B:
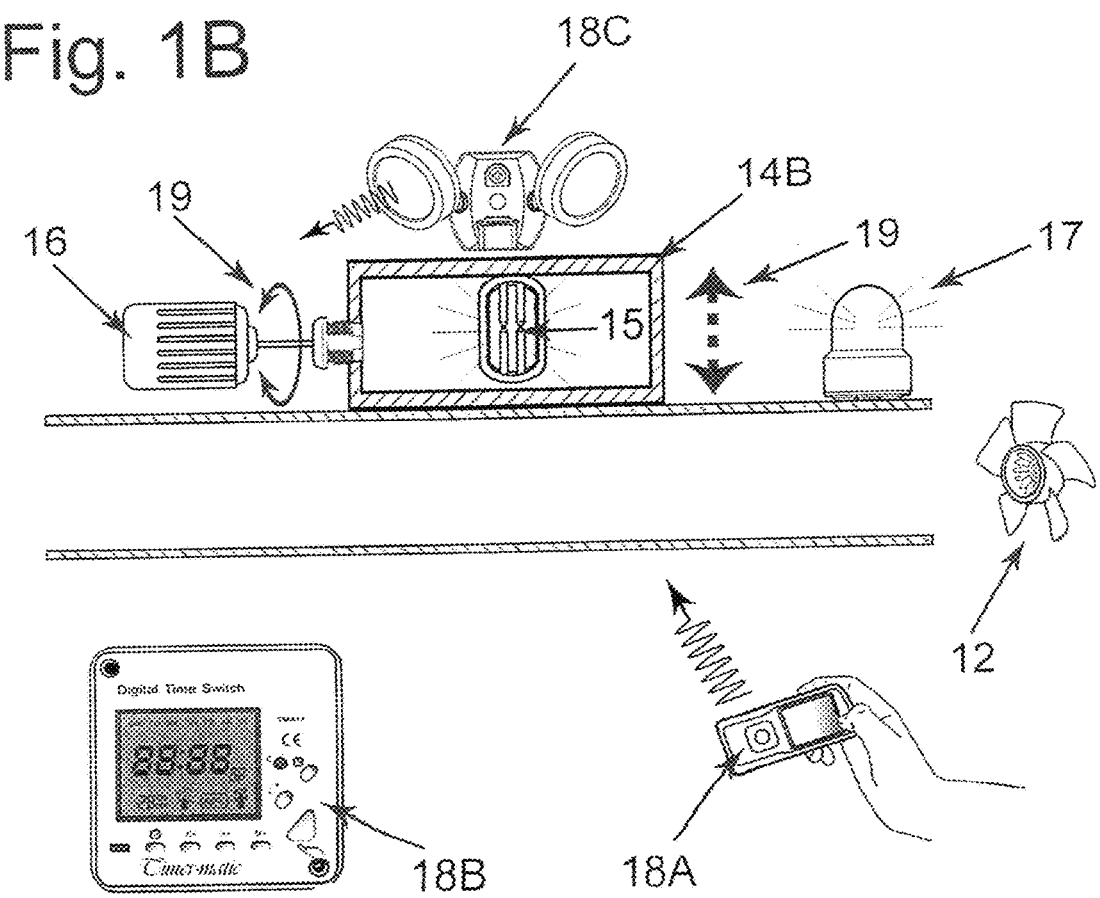

FIGS. 1A and 1B illustrate the preferred embodiment of the invention.

The apparatus 10 is divided into three basic sections: a first end section 10A, a second end section 10B, and a treatment chamber 10C. Ambient air is pulled by fan 12 from the first end 10A through the treatment chamber 10C and then out through end 10B. While this illustration shows the fan 12 pulling the ambient air, in another embodiment, the fan 12 is located at the opposing end and pushes the air through apparatus 10.

Located with the treatment chamber 10C is UV light source 15 which, in this illustration is connected to panel 14A which can be raised to panel position 14B to expose the UV light source 15 to the room's environment.

UV adsorbing materials 11A and 11B are located near baffles 9A and 9B. Baffles 9A and 9b are structured to assure that the UV light from UV light source 15 is not allowed to exit apparatus 10. The UV adsorbing materials 11A and 11B also provide assurance that UV light does not escape from apparatus 10.

In this embodiment, when the room is empty of humans, pets, and plants, UV light source 15 is raised by motor 16 as indicated by arrows 19 to expose UV light source 15. In this position, the surfaces within the room are treated to UV rays for sterilization purposes.

Exposing the UV light source 15 by motor 16 is either remotely controlled 18A or is set to operate from a timer 18B. In like manner, closing 14B is also done by motor 16 which is controlled by remote 18A or timer 18B.

Because the UV rays are harmful to humans, this embodiment utilizes a variety of safety measures. When open 14B, light beacon 17 is activated (alternatively an audio alarm is sounded). Further, motion sensor 18C is also used to sense if a human is in the room and if so, the UV light source 15, using motor 16, is again positioned within apparatus 10.

To obtain a lengthened dwell time within the treatment container 10C, in this embodiment, fan 12 is operated for a short period to draw the ambient air into treatment chamber 10C and then allowed to rest there until fully treated when it will then be exhausted by fan 12.

Figure 2:
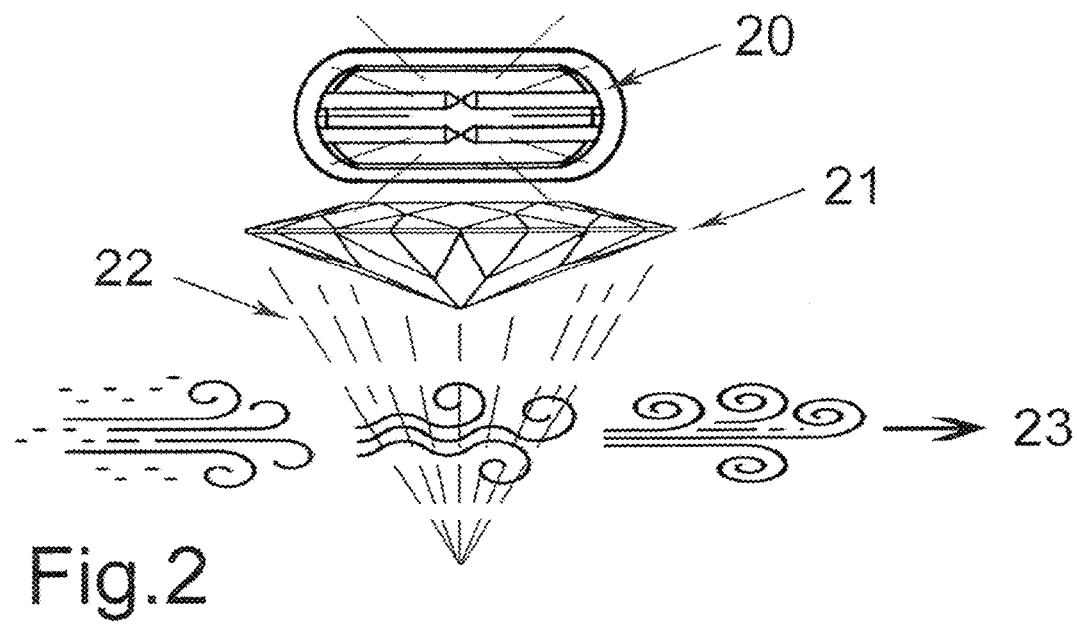
FIG. 2 illustrates the affect that magnifying glass has upon the concentration of UV light being applied to the ambient air stream.

FIG. 2 illustrates the affect that magnifying glass has upon the concentration of UV light being applied to the ambient air stream.

UV light source 20 is positioned so that it's emissions pass through magnifying lens 21 to focus, as illustrated 22, the focused rays onto ambient air stream 23. In this way, the concentrated UV rays have more impact upon the bacterium and viruses within ambient air stream 23.

Figure 3:
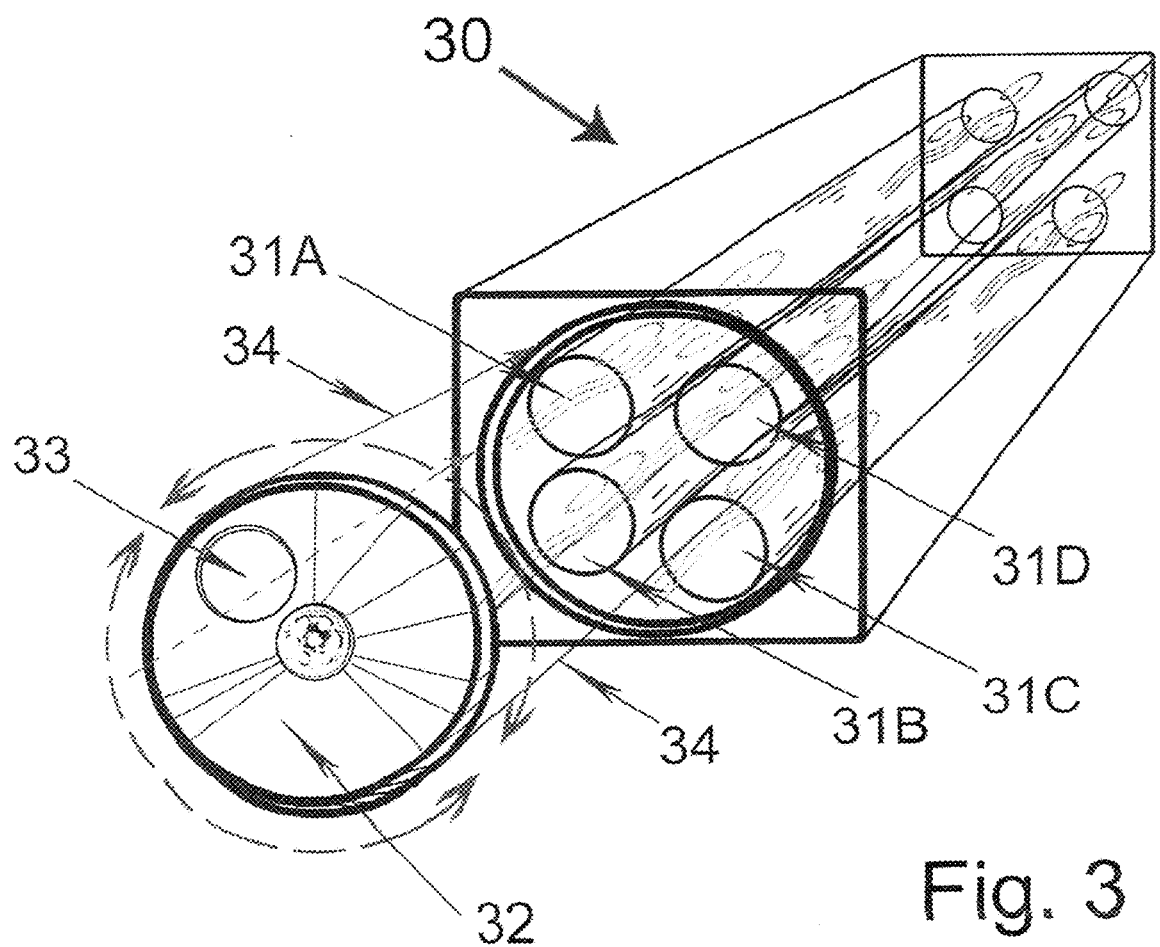
FIG. 3 illustrates the preferred embodiment for creating the desired dwell time.

FIG. 3 illustrates the preferred embodiment for creating the desired dwell time.

In this embodiment, within container 30 are four different channels/tubes 31A, 31B, 31C, and 31D, which are preferably made of glass or other transparent material allowing the UV rays (not shown) to penetrate to the ambient air flowing through the channels/tubes 31A, 31B, 31C, and 31D.

A fan (not shown for clarity purposes) draws the ambient air into the channels/tubes 31A, 31B, 31C, and 31D, but, the channels or tubes are periodically opened to the fan using plate 32 (mounted as indicated by arrows 34) which slowly rotates allowing portal 33 to selectively open/close a channel or tube. By controlling the speed of rotation of plate 32 and the length of the channels/tubes 31A, 31B, 31C, and 31D, the desired dwell time of the ambient air within is controlled.

It is clear that the present invention provides a continuously operating sterilizer.

What is claimed is:

1. A sterilizing apparatus comprising:
    a) A passage communicating ambient air therethrough, said passage having a treatment chamber therein and a first and second end sections, each end section configured to block light from the treatment chamber from escaping through the first end section and the second end section, wherein the treatment chamber has an open and a closed state, in the open state, ultraviolet light from the ultraviolet light source is permitted into the environment, in the closed state all ultraviolet light from the ultraviolet light source is contained within the treatment chamber;
    b) An ultraviolet light source located within the treatment chamber;
    c) a motor adapted to selectively move the treatment chamber between the open state and the closed state; and
    d) a timer mechanism for activation of the motor.

2. The sterilizing apparatus according to claim 1, wherein the ultraviolet light source generates light in the UV-C range.

3. The sterilizing apparatus according to claim 2, further including a coating of UV adsorbing material placed in the first end section and the second end section.

4. The sterilizing apparatus according to claim 3, wherein an interior portion of the treatment chamber is reflective of ultraviolet light.

5. The sterilizing apparatus according to claim 3, wherein an interior potion of the treatment chamber is mirror coated.

6. The sterilizing apparatus according to claim 3, further including a lens adapted to focus ultraviolet light from the ultraviolet source onto ambient air flowing through the treatment chamber.

7. The sterilizing apparatus according to claim 1, further including an alarm activated when the treatment chamber is in an open state.

8. The sterilizing apparatus according to claim 7, wherein the alarm is visual.

9. The sterilizing apparatus according to claim 1, further including a motion sensor and wherein the motion sensor activates a motor so that the treatment chamber is moved to a closed state when activity within the environment is sensed.

10. The sterilizing apparatus according to claim 1, further including an operator controller for activating the motor.

11. The sterilizing apparatus according to claim 3, wherein ambient air is drawn through the treatment chamber for a pre-selected period of activation and is idle between such periods of activation.

12. The sterilizing apparatus according to claim 3, further including:
   a) at least two ultraviolet light permeable channels through the treatment chamber; and,
   b) Dampening apparatus for selectively restricting flow of ambient air through all but one of the ultraviolet light permeable channels.

13. The sterilizing apparatus according to claim 12, wherein the dampening apparatus includes a motor rotating a plate having an opening therethrough, said plate being positioned at an end of the at least two ultraviolet light permeable channels.

14. The sterilizing apparatus according to claim 13, wherein a rotation of the plate is chosen to obtain a desired dwell time of the ambient air within each of the at least two ultraviolet light permeable channels.

\* \* \* \* \*